(12) United States Patent
Acher et al.

(10) Patent No.: US 8,771,373 B2
(45) Date of Patent: Jul. 8, 2014

(54) EPILATORY COMPOSITIONS

(75) Inventors: David Acher, Beverley (GB); Marielle De La Torre, Beverley (GB)

(73) Assignee: Reckitt Benckiser (UK) Limited, Slough, Berkshire (GB)

( * ) Notice: Subject to any disclaimer, the term of this patent is extended or adjusted under 35 U.S.C. 154(b) by 849 days.

(21) Appl. No.: 11/597,071

(22) PCT Filed: May 4, 2005

(86) PCT No.: PCT/GB2005/001676
§ 371 (c)(1),
(2), (4) Date: May 21, 2007

(87) PCT Pub. No.: WO2005/112876
PCT Pub. Date: Dec. 1, 2005

(65) Prior Publication Data
US 2008/0118457 A1 May 22, 2008

(30) Foreign Application Priority Data
May 20, 2004 (GB) .................................. 0411205.8

(51) Int. Cl.
*C14C 1/06* (2006.01)
(52) U.S. Cl.
USPC ......................................................... 8/94.16
(58) Field of Classification Search
None
See application file for complete search history.

(56) References Cited

U.S. PATENT DOCUMENTS

| 2,425,696 A | * | 8/1947 | Herrmann et al. ................ 8/160 |
| 5,154,919 A | * | 10/1992 | Des Garets ..................... 424/73 |
| 2003/0003118 A1 | | 1/2003 | Boilen et al. |

FOREIGN PATENT DOCUMENTS

| EP | 1 245 220 A1 | 10/2002 |
| FR | 2 656 524 A1 | 7/1991 |
| FR | 2 751 873 A1 | 2/1998 |
| FR | 2798064 | 3/2001 |
| FR | 2 823 666 A1 | 10/2002 |
| GB | 474102 | 10/1937 |
| GB | 2 336 535 | 10/1999 |
| GB | 2 385 269 | 8/2003 |
| GB | 2 391 475 A | 2/2004 |
| WO | WO 02/11687 A2 | 2/2002 |
| WO | 02/085318 | 10/2002 |

OTHER PUBLICATIONS

PCT International Search Report, PCT/GB2005/001676, dated Aug. 8, 2005.
PCT International Written Opinion, PCT/GB2005/001676, dated Aug. 8, 2005.
GB Search Report, GB 0411205.8, dated Aug. 27, 2004.
PCT International Preliminary Report on Patentability, PCT/GB2005/001676, dated Nov. 21, 2006.
Remington's Pharmaceutical Sciences, Seventeenth Edition, 1985, p. 1317.

* cited by examiner

*Primary Examiner* — Trevor Love
(74) *Attorney, Agent, or Firm* — Troutman Sanders LLP; Ryan A. Schneider

(57) ABSTRACT

An epilatory composition of the adhesive type comprises: a. from 50 to 90 percent by weight of a rosinous material or hydrocarbon resin; b. from 0.5 to 20 percent by weight of water, and c. an emulsifier and/or surfactant. The composition is particularly suitable for heating, prior to application to the skin, in a domestic microwave oven.

13 Claims, No Drawings

EPILATORY COMPOSITIONS

The present invention relates to an epilatory composition, and to its use for removal of unwanted hair from humans.

Epilatory compositions formed of viscoelastic materials are well known. Known viscoelastic materials include those which are rosin-based. In some products the epilatory compositions may be supplied in the form of strips, retained between cellophane or non-woven sheets. In use, the user peels away one of the sheets, presses the epilatory strip firmly onto the area to be plucked, then pulls one end of the remaining cellophane sheet sharply away from the area. The hairs trapped in the composition are removed from the treated area along with, optimally, all of the composition, still attached to the remaining backing strip.

In another approach a composition may be warmed, and then applied to the skin, for example by means of a spatula or other applicator. Strips of fabric or a non-woven material are then applied so that they adhere to the epilatory composition. The strips are then pulled sharply to remove the epilatory material and hair from the skin.

In a yet further approach a composition may again be warmed and applied to the skin, for example by means of a spatula or other applicator. The composition is then allowed to set or harden and then pulled sharply to remove the epilatory material and hair from the skin without the necessity of applying a strip of fabric.

In the latter two approaches it is often a requirement that the composition is first warmed. Warming can be conducted in a variety of ways, for example by placing a container containing the composition in a pan of hot water, into a microwave oven or into an appropriate electrical heating device. However, that when an oven such as a microwave oven is used the user must adhere strictly to the heating instructions to ensure that the composition does not become overheated. There is no visible indication of overheating. Furthermore a microwave oven may not heat the composition consistently throughout and one or more hot regions or hot spots may develop. These are potentially dangerous since the composition may appear to have an appropriate temperature, but when it is applied to the skin the hot spots may burn the skin.

EP 1 245 220 discloses an epilatory wax comprising a wax base mixed with an aqueous solution and a surfactant.

We have now found a composition and method which simultaneously provides a visible indication when the wax is too hot to be safely applied to the skin and has a more homogenous melt pattern, leading to lower risk of hot-spots, particularly when heated in a microwave oven, and yet still retains the ability to remove hairs including short hairs.

The present invention provides an epilatory composition of the adhesive type which comprises:
 a. from 50 to 90 percent by weight of a rosinous material or hydrocarbon resin;
 b. from 0.5 to 20 percent by weight of a hydroxy-group containing compound selected from water, glycerine, polyethylene glycol and mixtures thereof; and
 c. an emulsifier and/or surfactant.

The present invention also provides a method for removing hair from skin which comprises:
 a. heating a composition as defined above;
 b. applying said composition to the skin;
 c. allowing said composition to set and hold said hair or applying a strip of material over said composition and allowing said strip to adhere thereto; and
 d. removing said composition and hair by peeling said composition or said material and said composition, from the skin.

Preferably, the method is carried out with the heating of the composition carried out in a domestic microwave oven.

It has surprisingly been found that the composition of the present invention can be heated in a microwave oven without the formation of very hot regions or very hot spots, for example having a temperature of 120° C. or above under normal heating conditions when the average temperature of the composition is about 60° C. It may also be possible to heat the composition to the required temperature in a shorter period of time. In particular it may be heated such that some of the composition, for example about 60%, is melted, for example reaching a maximum temperature of about 75° C., and the remainder is merely softened. The composition can then be stirred by a user to form a homogenous composition before it is applied to the skin. In prior compositions a very hot, liquid phase reaching a maximum temperature of higher than 110° C., for example constituting about 30% of the composition, could be formed with some of the composition remaining solid, particularly at the edges of the composition. This could make homogenisation of the composition both difficult and unsafe.

The composition of the present invention also has a further advantage in that the when the hydroxy-group containing compound comprises high levels, suitably 50% or more by weight of water, which is present as droplets distributed through the composition, this begins to bubble when it is heated too much, for example when the composition temperature exceeds about 80° C. This acts as a good visual indication to the user that the composition is too hot to be applied safely to the skin.

The rosinous material may be, for example, rosin and/or a rosin based material. Preferably the rosin material is a rosin ester and/or colophony. The hydrocarbon resin may be, for example, a terpene resin, a cyclic aliphatic hydrocarbon resin and/or a polycyclopentadiene. One or more rosinous materials or hydrocarbon resins may be used. It is also possible to use a mixture of at least one rosinous material and at least one hydrocarbon resin.

The composition of the present invention desirably comprises at least 50 percent by weight of the rosinous material or hydrocarbon resin, preferably at least 60 percent by weight. Generally the composition comprises less than 90 percent by weight of the rosinous material or hydrocarbon resin, and preferably less than 80 percent by weight.

The composition of the present invention must comprise a hydroxy-group containing compound selected from water, glycerine, polyethylene glycol and mixtures thereof. The hydroxy-group containing compound is able to absorb microwave energy.

The hydroxy-group containing compound may be blended with other hydroxy-group containing compounds such as sugar waxes or polyvinyl alcohol.

The composition comprises the hydroxy-group containing compound in an amount of from 0.5 to 20 percent by weight based on the entire weight of the composition, excluding any container in which it is held. Preferably the hydroxy-group containing compound is present in an amount of from 1 to 20 percent by weight, more preferably from 1 to 15 percent by weight, even more preferably from 1 to 10 percent by weight, yet more preferably from 1 to 7 percent by weight, and most preferably from 2 to 5 percent by weight.

The composition of the present invention also comprises an emulsifier and/or surfactant. These ensure that there is a degree of physical stability against phase separation between the rosinous material and/or hydrocarbon resin and any further hydrophobic components which may be present, and the water.

If the hydroxy-group containing compound is polyethylene glycol, it suitably has a molecular weight of 4000 or less, preferably 1000 or less, more preferably 400 or less. Preferably, the hydroxy-group containing compound is water or glycerine (glycerol) or mixtures thereof. It is particularly preferred if the hydroxy-group containing compound is water.

In addition the emulsifier and/or surfactant may act as a plasticizer for the composition making it easier to handle it safely at high temperatures.

Suitable emulsifiers are polyethylene glycol hydrogenated castor oil such as PEG-40 hydrogenated castor oil and polycaprolactones.

The surfactant may be, for example, a nonionic, anionic, cationic, amphoteric or zwitterionic surfactant or mixture thereof. Examples of nonionic surfactants are alkoxylated fatty alcohols such as fatty alcohols containing from 8 to 18 carbon atoms, especially from 12 to 16 carbon atoms, with from 2 to 10 ethoxy groups, especially 3 to 7 ethoxy groups. A suitable ethoxylated fatty alcohol is Lutensol AO3. Further examples of surfactants as alcohol-oil transesterified surfactants such as PEG hydrogenated oils, sorbitan fatty acid esters, polyethylene glycol sorbitan fatty acid esters, sterol and sterol derivatives. Suitable surfactants are, for example, sorbitan monostearate, sorbitan laurate, sorbitan mono-oleate, sorbitan oleate, PEG-40 hydrogenated castor oil and polyglyceryl-3-ricinoleate. PEG-40 hydrogenated castor oil has been found to give particularly low risk of hot-spots, especially when used with water as the hydroxy-group containing compound.

The composition of the present invention comprises from 0.2 to 16 percent by weight, preferably 2 to 15 percent by weight of the emulsifier and/or surfactant, more preferably from 3 to 10 percent by weight.

The composition of the present invention may comprise, if desired, further components such as a wax, elastomer and/or particulate material.

It is particularly desirable for the composition of the present invention to comprise at least one wax. Examples of suitable waxes are natural waxes such as beeswax, lanolin and hydrocarbon waxes such as microcrystalline wax or paraffin wax. Desirably a mixture of at least one natural wax and at least one synthetic wax are used. A suitable wax is, for example, Licowax KSL obtainable from GE Silicones.

The wax is preferably present in the composition of the present invention in an amount of up to 40 percent by weight, more preferably from 5 to 40 percent by weight even more preferably from 10 to 30 percent by weight A particularly preferred further ingredient in compositions of the invention is an elastomeric polymer. Examples of elastomeric polymers are styrene copolymers such as styrene-butadiene and styrene-isoprene copolymers; ethylene-propylene copolymers; ethylene-propylene terpolymers; vinyl ethylene-acetate copolymers, acrylic polymers; butadiene, isoprene, isoprene-isobutene, isobutene and chloroprene elastomers; nitrile rubbers and polyester thermoplastic elastomers. Further details of such elastomers may be found in, for example, U.S. Pat. No. 5,154,919.

A particularly preferred elastomer for use in compositions of the invention, as it provides excellent short hair removal, is an elastomer selected from styrene-butadiene and styrene-isoprene copolymers and mixtures thereof.

Desirably the composition comprises up to 10 percent by weight of the elastomer, preferably from 1 to 10 percent by weight, more preferably from 2 to 4.4 percent by weight.

The composition of the present invention may also comprise a particulate material such as a colloidal material. Preferably the particles have a mean diameter of from 1 nm to 100 μm, more preferably from 5 nm to 10 μm, and most preferably from 10 nm to 1 μm. Preferably the particles are solid at 20° C.

If the particles are present in the epilatory composition, they are preferably present in an amount of at least 0.5 percent by weight, more preferably at least 1 percent by weight, and most preferably at least 2 percent by weight. Suitably they are present in an amount of less than 40 percent by weight, preferably less than 20 percent by weight, and most preferably less than 10 percent by weight.

Preferred particulate materials for use in the present invention are mineral materials. Especially preferred is titanium dioxide or amorphous silica.

The composition may suitably comprise a further component such as a fragrance, a polymer, an essential oil, a silicone oil, a colorant, an anti-oxidant and/or a paraffin and/or mineral oil. Desirably these further components are present in a total amount of up to 10 percent by weight of the composition, preferably up to 5 percent by weight.

Preferably the compositions of the present invention are such that residues are removable from the user's-skin by washing with an oily material such as paraffin oil or propylene glycol.

The compositions of the present invention may be prepared by suitable method. For example the rosinous material or hydrocarbon resin is melted, optionally together with any wax. Separately water is mixed with the emulsifier and/or surfactant, added to the molten rosinous material or hydrocarbon resin and mixed in till the composition is homogeneous. It is usual for both phases to have the same or a similar temperature when they are mixed with each other.

When it is desired to be used, the composition of the present invention may simply be heated. Heating may be carried out by any means such as by placing a container comprising the composition in a bath of hot water, such as a saucepan of boiling water. Most desirably, however, the composition of the present invention can be heated in an oven or a microwave oven. The length of time that the composition must be heated will depend on a number of factors, including the quantity of composition to be heated, the nature of the container in which it is held and the power of the microwave oven. Suitable heating instructions may be provided in association with a container comprising the composition. Another aspect of the invention concerns a microwaveable container comprising a composition as detailed herein for use in the methods described herein.

Once the composition has been warmed it may be stirred, if desired, in particular to ensure a more uniform temperature throughout the composition. It may then be applied by a user to the skin, for example using a spatula or applicator.

The composition is then allowed to set on the skin and hold the hair, or a strip of material such as a fabric can be applied over the composition and allowed to adhere thereto. The composition or the fabric together with the composition can then be pulled or peeled from the skin in order to remove the hair therefrom.

The present invention will now be further described in the following Examples.

EXAMPLE 1

A composition having the following formulation was prepared:

| | |
|---|---|
| Glyceryl rosinate | 63.8 wt % |
| Paraffin wax | 13.8 wt % |
| Beeswax | 7.5 wt % |
| EVA Copolymer (28-800) | 4.4 wt % |
| Liquid paraffin oil | 0.5 wt % |
| PEG-40 hydrogenated castor oil | 7 wt % |
| Water | 3 wt % |

The two waxes were first melted, and stirring was started carefully when the temperature reached 70 to 75° C. When the temperature reached 100 to 110° C., quarter of the glycerol rosinate was added, allowed to melt, and further quarters added until it had all been added. Afterwards the EVA copolymer was added at 110° C. The mixture was then stirred until the composition was molten. This took about 30 minutes at 110 to 120° C.

The mixture was then cooled to 60 to 65° C. and held at this temperature for the remainder of the preparation process.

Separately the PEG-40 hydrogenated castor oil and water were mixed together in another vessel and heated to the same temperature as the resin base mixture, i.e. 60 to 65° C., while stirring intermittently. It was then added slowly to the resin base mixture with stirring. The mixture was then stirred for 20 minutes to ensure a homogeneous composition, and filled into jars in individual amounts of 300 g.

EXAMPLE 2

A composition having the following formulation was prepared:

| | |
|---|---|
| Glyceryl rosinate | 63.8 wt % |
| Paraffin wax | 13.8 wt % |
| Beeswax | 7.5 wt % |
| EVA Copolymer (28-800) | 4.4 wt % |
| Liquid paraffin oil | 0.5 wt % |
| PEG-40 hydrogenated castor oil | 7 wt % |
| Water | 1.5 wt % |
| Glycerin | 1.5 wt % |

The composition was prepared in the same way as the composition of Example 1.

EXAMPLE 3

A composition having the following formulation was prepared:

| | |
|---|---|
| Glyceryl rosinate | 64.2 wt % |
| Paraffin wax | 13.6 wt % |
| Beeswax | 7.3 wt % |
| Styrene-isoprene-styrene copolymer | 3.6 wt % |
| Liquid paraffin oil | 0.5 wt % |
| Titanium dioxide | 1.8 wt % |
| PEG-40 hydrogenated castor oil | 5 wt % |
| Water | 3 wt % |
| Silica | 1 wt % |

The composition was prepared in the same way as the composition of Example 1.

COMPARATIVE EXAMPLE 1

A composition having the following formulation was prepared:

| | |
|---|---|
| Glyceryl rosinate | 70.9 wt % |
| Paraffin wax | 15.4 wt % |
| Beeswax | 8.4 wt % |
| EVA copolymer (28-800) | 4.9 wt % |
| Liquid Paraffin oil | 0.5 wt % |

This composition is the same as the composition of Example 1 except that the water and the emulsifier are omitted. The composition was prepared in the same way as the composition of Example 1 except that after the EVA copolymer was added and stirred into the composition until the copolymer was molten, taking about 30 minutes at 100 to 120° C., the mixture was cooled to 80° C. before filling the jars.

The composition of Example 1 was heated at half power in a 900 W Whirlpool microwave. It was usable after 120 seconds, having a maximum temperature of about 68° C. After the composition was overheated by continuing to heat it for 210 seconds it started to bubble and boil at a maximum temperature of about 100° C.

The composition of Comparative Example 1 was heated at full power in a 900 W Whirlpool microwave. The composition was usable after 120 seconds, having a maximum temperature of about 146° C., indicating the formation of very hot regions. After the composition was overheated by continuing to heat it for 210 seconds, there was no visual indication of overheating, and it had a maximum temperature of about 150° C.

The invention claimed is:

1. An epilatory composition of the adhesive type which comprises:
   a. from 50 to 90 percent by weight of a rosinous material or hydrocarbon resin;
   b. from 0.5 to 20 percent by weight of a hydroxy-group containing compound selected from water, glycerol, polyethylene glycol and mixtures thereof;
   c. an emulsifier and/or surfactant;
   d. a mixture of at least one natural wax and one synthetic wax; and
   e. from 2 to 4.4 percent by weight of an elastomeric polymer that is vinyl ethylene-acetate copolymer.

2. A composition according to claim 1 which comprises from 1 to 7 percent by weight of the hydroxy-group containing compound.

3. A composition according to claim 1 wherein the hydroxy-group containing compound is water.

4. A composition according to claim 1, which comprises from 0.2 to 16 percent by weight of the emulsifier and/or surfactant.

5. A composition according to claim 1, which comprises from 5 to 40 percent by weight of wax.

6. A microwaveable container comprising a composition as defined in claim 1.

7. A method for removing hair from skin which comprises:
   a. heating a composition as defined in claim 1;
   b. applying said composition to the skin;
   c. allowing said composition to set and hold said hair or applying a strip of material over said composition and allowing said strip to adhere thereto; and
   d. removing said composition and hair by peeling said composition or said material and said composition, from the skin.

8. A method according to claim 7 wherein said composition is heated by microwaves.

9. The composition of claim 2, wherein the hydroxy-group containing compound is water.

10. The composition of claim 2, comprising from about 0.2 to about 16 percent by weight of the emulsifier and/or surfactant.

11. The composition of claim 3, comprising from about 0.2 to about 16 percent by weight of the emulsifier and/or surfactant.

12. An epilatory composition of the adhesive type which comprises:
- from 50 to 90 percent by weight of a rosinous material or hydrocarbon resin;
- from 0.5 to 20 percent by weight of a hydroxy-group containing compound selected from water, glycerol, polyethylene glycol and mixtures thereof; and
- an emulsifier and/or surfactant;
- a mixture of at least one natural wax and one synthetic wax; and
- from 2 to 4.4 percent by weight of an elastomeric polymer that is vinyl ethylene-acetate copolymer; and
- wherein the composition comprises up to 40 percent by weight of wax.

13. An epilatory composition of the adhesive type which comprises:
- from 50 to 90 percent by weight of a rosinous material or hydrocarbon resin;
- from 0.5 to 20 percent by weight of a hydroxy-group containing compound selected from water, glycerol, polyethylene glycol and mixtures thereof; and
- an emulsifier and/or surfactant;
- a mixture of at least one natural wax and one synthetic wax; and
- from 2 to 4.4 percent by weight of an elastomeric polymer that is vinyl ethylene-acetate copolymer;
- wherein the composition comprises up to 40 percent by weight of wax, and wherein the composition comprises from about 0.2 to about 16 percent by weight of the emulsifier and/or surfactant.

* * * * *